United States Patent [19]

Joyeau et al.

[11] Patent Number: 5,030,628
[45] Date of Patent: Jul. 9, 1991

[54] N-ARYL-AZETIDINONES, THEIR PREPARATION PROCESS AND THEIR USE AS ELASTASE INHIBITORS

[75] Inventors: Roger Joyeau; Randa Kobaiter; Michel Wakselman; Michèle Reboud, all of Paris, France

[73] Assignee: Scientifique, Paris, France

[21] Appl. No.: 452,774

[22] Filed: Dec. 19, 1989

[30] Foreign Application Priority Data

Dec. 19, 1988 [FR] France ............................ 88 16732

[51] Int. Cl.$^5$ ................. A61K 31/395; C07D 205/08; C07F 9/568; C07F 7/18
[52] U.S. Cl. .................... 514/210; 514/825; 514/824
[58] Field of Search ...................... 540/362, 200, 362; 514/210

[56] References Cited

U.S. PATENT DOCUMENTS 4,680,391 7/1987 Firestone ............................ 540/362
4,803,266 2/1989 Kawash ............................ 540/200

OTHER PUBLICATIONS

Stirling, Ed, "The Chemistry of the Sulphonium Group", pp. 269, 267 (1981).
Zrihen, European Journal of Medicinal Chemistry, vol. 18, No. 4, 1983, pp. 307–314.
Ongania, Zeitschrift Fur Naturforschung, vol. 49b, No. 1, part B, Jan. 1985, pp. 115–116.

Primary Examiner—Mark L. Berch
Attorney, Agent, or Firm—Pearne, Gordon, McCoy & Granger

[57] ABSTRACT

The invention relates to N-aryl-azetidinones, their preparation process and their use as active serine elastase inhibitors.

The N-aryl-azetidinones are in accordance with formula:

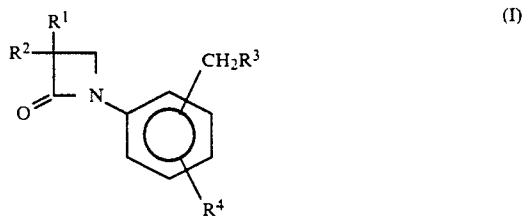

in which $R^1$ and $R^2$ can be a halogen atom or an organic radical, $R^3$ represents a halogen atom or another good starting group and $R^4$ represents H or an organic radical.

The compounds with $R^3$=Cl or $OSO_2CH_3$, $R^4$=H and $R^1$=$R^2$=F or $R^1$=F and $R^2$=Br are irreversible and selective elastase inhibitors.

13 Claims, No Drawings

N-ARYL-AZETIDINONES, THEIR PREPARATION PROCESS AND THEIR USE AS ELASTASE INHIBITORS

The present invention relates to novel-aryl-azetidinones, their preparation process and their use as active serine elastase inhibitors.

It more specifically relates to N-aryl-azetidinones functionalized by appropriate substituents giving them selectivity properties with respect to elastases, particularly leucocytic elastase and pancreatic elastase and giving them the capacity to inhibit these elastases in an irreversible manner.

The non-equilibrium between the concentrations of the elastases and their natural macromolecular inhibitors leads to numerous pathological processes.

Thus, the increased deterioration of the elastin of the conjunctive tissue and cartilages by leucocytic elastase is involved in pulmonary emphysema, rheumatoid arthritis, various other inflammatory processes and in cutaneous ageing.

In addition, research has been carried out to find irreversible synthetic inhibitors for leucocytic elastase able to remedy the deficiency or ineffectiveness of natural inhibitors and which would therefore have great interest in therapy. Synthetic inhibitors of this type are described by W. C. Groutas in Med. Res. Review, 1987, 7, No. 2, pp. 227-241 and by Trainor in Trends in Pharmacological Sciences, August 1987, Vol. 8, No. 8, pp. 303-307.

These inhibitors include modified cephalosporins, which are able to inhibit human leucocytic elastase, as is described by Doherty et al in Nature, Vol. 322, 1986, pp. 192-194 and by Navia et al in Nature, Vol. 327, 1987, pp. 79-82. These cephalosporins are in accordance with the following formula:

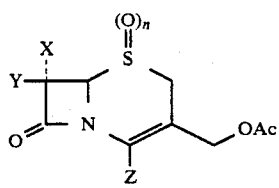

in which X can be an atom of hydrogen, fluorine or chlorine or other radicals, such as alkoxy, aryl, CH$_3$CONH, CF$_3$CONH or HCONH radicals, Y can be an atom of hydrogen or other organic radicals and Z is a carboxyl, ester or amide radical or a hydrogen atom.

Zrihen et al in Eur. J. Med. Chem.—Ther., 1983, 18, No. 4, pp. 307-314 describe a possible mechanism for the irreversible deactivation of β-lactamases by functionalized N-aryl-azetidinones. However, the results of Table 1 show that the halomethylated derivatives of N-aryl-azetidinones having a latent electrophilic function are not irreversible inhibitors, but competitive inhibitors of said enzymes.

Subsequent research carried out on certain activated N-aryl-azetidinones demonstrated that these compounds could also be competitive inhibitors of β-lactamases, as is described by Joyeau et al in Journal of Medicinal Chemistry, 1988, Vol. 31, No. 2, pp. 370-374.

The latter N-aryl-azetidinones are in accordance with the formula:

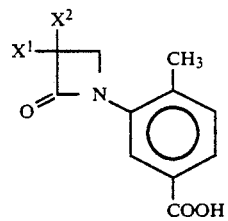

In which $X_1$ and $X_2$ can represent Br and H, Br and F, F and H or F and F.

These compounds have an affinity for beta-lactamase, but they are not substrates of this enzyme.

The present invention relates to novel substituted N-aryl-azetidinones, which have the property of being irreversible inhibitors of active serine elastases, such as leucocytic elastase and pancreatic elastase.

According to the invention the N-aryl-azetidinones according to the formula:

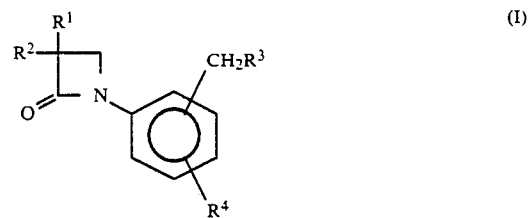

in which $R^1 R^2$, which can be the same or different, represent an atom of F, Dr, Cl or I or a radical of formula CF$_3$, COOR$^5$, CN, CONHR$^5$ or COR$^5$ with R$^5$ representing an alkyl or aryl radical, R$^3$ represents a fluorine, chlorine, bromine or iodine atom, or a radical of formula OC(O)R$^6$, OSO$_2$R$^6$, OP-(O)R$^6_2$ or S+R$^6_2$ with R$^6$ representing an alkyl, perfluoroalkyl or aryl radical and R$^4$ represents a hydrogen atom or a radical chosen from among the alkyl radicals and the radicals of formula COOR$^7$, CONHR$^7$, NO$_2$, CF$_3$, CN,SO$_2$R$^7$, (CH$_2$)$_n$OR$^7$ and OR$^7$ with R$^7$ representing a hydrogen atom or an alkyl or aryl radical and n being an integer between 1 and 18.

In the formula of the N-aryl-azetidinones according to the invention, the choice of the substituents R$^1$, R$^2$ and R$^3$ makes it possible on the one hand to give the molecule a selectivity relative to elastases compared with other proteases and on the other hand make it serve the function of the suicide inhibitor. The action mechanism as the inhibitor probably corresponds to the unmasking of the latent electrophilic function and the substitution by a nucleophilic residue present in the active centre, in accordance with the following diagram:

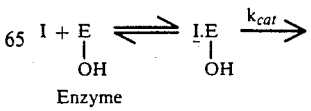

Enzyme

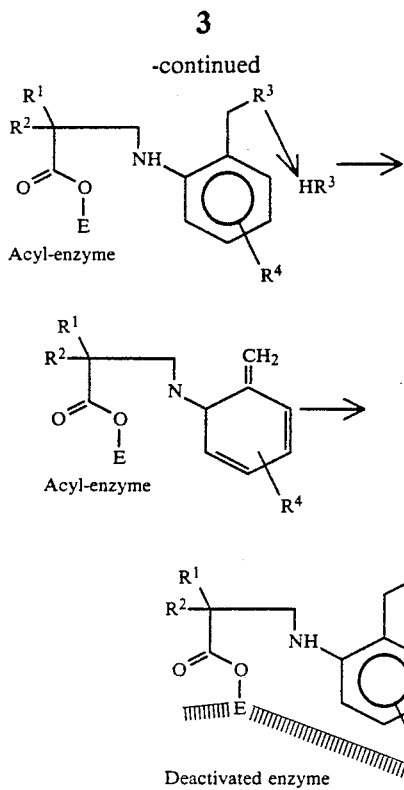

Acyl-enzyme

Acyl-enzyme

Deactivated enzyme

Thus, in the acyl-enzyme, the aminobenzyl halide has a good starting group, so that $R^3$ is very reactive. The substitution by a nucleophilic residue Nu of the active centre of the enzyme takes place rapidly by a dissociative mechanism (elimination-addition) with as the intermediary a methylene quinonimine. The inhibitor is retained in the active centre, as a result of the covalent connection, throughout the life of the acylenzyme. The alkylation of the residue Nu consequently leads to an irreversible inhibition of the elastase.

In this mechanism of the "suicide" type, the reactive function is latent and is only released during the catalytic process of the target enzyme within the active centre, which considerably limits the possibility of reactions between the inhibitor and other compounds present on its path in vivo.

In order that the N-aryl-azetidinones in question can serve as a suicide inhibitor, it is necessary for the $-CH_2R^3$ substituent to be in the ortho or para position relative to N. Preferably the $-CH_2R^3$ substituent is in the ortho position relative to N.

Although $R^4$ can represent several substituents, good results can be obtained when using a hydrogen atom for $R^4$.

The substituents $R^3$ used in the invention are chosen so as to constitute good starting groups favouring the substitution mechanism by a nucleophilic residue. Good results are obtained when $R^3$ represents Cl or $OSO_2CH_3$.

When the N-aryl-azetidinones according to the invention are not used as elastase inhibitors, $R^3$ can represent a fluorine atom. Such N-aryl-azetidinones can in particular be used as elastase substrates.

In the invention, $R^1$ and $R^2$ are chosen so as to give the N-aryl-azetidinone a selectivity with respect to the elastases to be inhibited. For example, when the elastase is leucocytic or pancreatic elastase, $R^1$ and $R^2$ can both represent a fluorine atom or $R^1$ can represent a fluorine atom and $R^2$ a bromine atom.

In the invention, the alkyl or perfluoroalkyl radicals used for $R^5$ and $R^6$ can be straight or branched radicals and generally have 1 to 18 carbon atoms.

When $R^5$ or $R^6$ represents an aryl radical, the latter can have 6 to 14 carbon atoms. As an example of such radicals, reference can be made to phenyl and naphthyl radicals.

When in the invention $R^4$ or $R^7$ represents an alkyl radical, the latter can be straight or branched. In general, use is made of an alkyl radical with 1 to 18 carbon atoms. When $R^7$ represents an aryl radical, it is possible to use the aryl radicals described hereinbefore.

The N-aryl-azetidinones of the invention complying with formula (I) can be prepared by conventional processes. For example, it is firstly possible to prepare a N-aryl-azetidinone of formula:

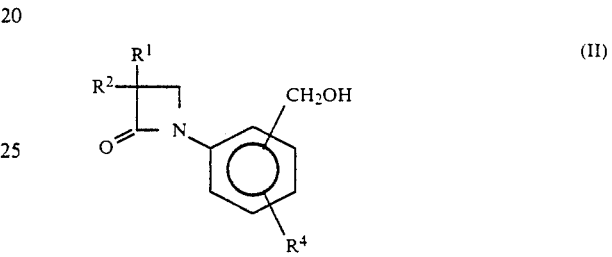

(II)

in which $R^1$, $R^2$ and $R^4$ have the meanings given hereinbefore, in order to transform said N-aryl-azetidinone of formula (II) into N-aryl-azetidinone of formula (I) by reaction with an appropriate reagent chosen as a function of the $R^3$ group to be introduced.

The N-aryl-azetidinone of formula (II) can be prepared:

a) by reacting a β-halogenopropanoyl halide of formula:

$$X^1OC-C(R^1R^2)-CH_2X^2 \qquad (III)$$

in which $X^1$ represents F, Cl, Br or I, $X^2$ represents Cl, Br or I and $R^1$ and $R^2$ have the meanings given hereinbefore, with a silyloxymethylaniline of formula:

(IV)

to obtain a halopropionanilide of formula:

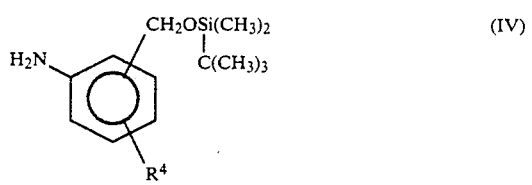

(V)

and then
b) by forming a N-aryl-azetidinone of formula:

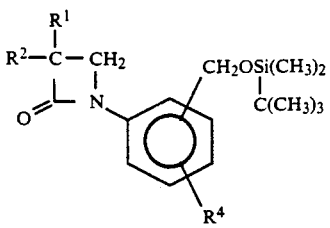

by the cyclization of said halopropionanilide of formula (V) and c) transforming said N-aryl-azetidinone of formula (VI) into N-aryl-azetidinone of formula (II) by reacting with a mixture of hydrofluoric acid and water.

As has been shown hereinbefore, the reagent for transforming the N-aryl-azetidinone of formula (II) into N-aryl-azetidinone of formula (I) is dependent on the substituent $R^3$ to be introduced. When $R^3$ represents Cl, the reagent used can be $SOCl_2$. When $R^3$ represents F, the reagent used can be diethylamino sulphur trifluoride. When $R^3$ represents Br or I, the reagent used can be $PBr_3$, $SOBr_2$, $R_3SiX (X=Br$ or $I$ and $R=alkyl)$, $\phi_3P + I_2 +$ imidazole.

When $R^3$ represents $OC(O)R^6$, $OSO_2R^6$ or $OPOR^6{}_2$, it is possible to use as the reagents the chlorides or anhydrides of the corresponding acids. For example, for introducing a substituent $R^3$ of formula $OSO_2R^6$, it is possible to use as the reagent $ClSO_2R^6$. When $R^3$ represents $S^+R^6{}_2$ the reagent used can be that of the corresponding halogenated derivative with a dialkyl sulphide.

The starting reagents used for the preparation of N-aryl-azetidinones are commercially available products, or can be prepared by standard processes.

For example, the beta-bromopropanoyl halides of formula (III) can be prepared from esters of formula $BrCH_2COCO_2C_2H_5$ by fluorination and/or chlorination reactions. They are described in J. Med. Chem. 1988, 31, p.370 in the case where X is Cl and $R^1$ and $R^2$ are F. In the case where X is Br and $R^1$ and $R^2$ are respectively Br and F, it is possible to use the process described by Molines et al in Synthesis, 1985, p.755.

The silyloxymethylanilines of formula (IV) can be prepared from the corresponding aminobenzyl alcohols by reacting with a silyl halide in the presence of imidazole.

The N-aryl-azetidinones of formula (I) in which $R^3$ is a bromine atom and $R^4$ represents a hydrogen atom or a radical chosen from among the radical of formula $COOR^7$, $CONHR^7$, $NO_2$, $CF_3$, CN and $SO_2R^7$ with $R^7$ representing a hydrogen atom or an alkyl or aryl radical and n being an integer between 1 and 18 can also be prepared by a process consisting of reacting a N-aryl-azetidinone of formula:

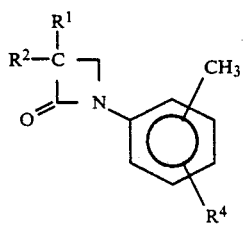

in which $R^1$, $R^2$ and $R^4$ have the meanings given hereinbefore with N-bromosuccinimide.

The N-aryl-azetidinone of formula (VII) used in the process can be prepared by a process identical to that used for N-aryl-azetidinone of formula (VI) by reacting a β-halogenopropanoyl halide according to formula (III) with a toluidine of formula:

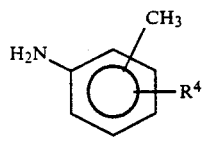

in which $R^4$ has the meaning given hereinbefore.

As has been shown hereinbefore, the N-aryl-azetidinones according to the invention can be used in pharmaceutical compositions as elastase inhibitors.

The present invention also relates to a pharmaceutical composition incorporating an elastase inhibitor, characterized in that said elastase inhibitor is a N-aryl-azetidinones according to the formula:

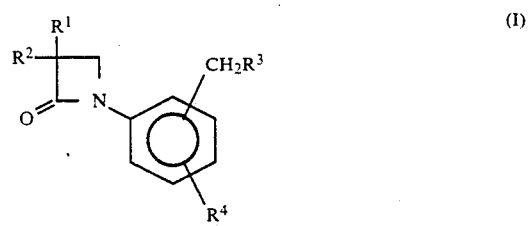

in which $R^1$ and $R^2$, which can be the same or different, represent an atom of F, Br, Cl or I, or a radical of formula $CF_3$, $COOR^5$, CN, $CONHR^5$ or $COR^5$ with $R^5$ representing an alkyl or aryl radical, $R^3$ represents a fluorine, chlorine, bromine or iodine atom, or a radical of formula $OC(O)R^6$, $OSO_2R^6$, $OP(O)R^6{}_2$ or $S^+R^6{}_2$ with $R^6$ representing an alkyl, perfluoroalkyl or aryl radical and $R^4$ represents a hydrogen atom or a radical chosen from among the alkyl radicals and the radicals of formula $COOR^7$, $CONHR^7$, $NO_2$, $CF_3$, CN, $SO_2R^7$, $(CH_2)_nOR^7$ and $OR^7$ with $R^7$ representing a hydrogen atom or an alkyl or aryl radical and n being an integer between 1 and 18.

These pharmaceutical compositions can be in the form of solutions, suspensions, powders or solubilizable granules, syrups or elixirs, auricular, nasal or ophthalmic drops, tablets, gelatin-coated pills, aerosols, ointments, transdermal applications or suppositories, in dosed presentations containing non-toxic supports, adjuvants and excipients. The injections can e.g. be intravenous, intramuscular, subcutaneous, intradermal, intrasternal or intra-articular. It is also possible to use infusion or instillation methods (e.g. intratracheal).

In order to more particularly target the pulmonary tissue, solutions containing albumin microspheres to which N-aryl-azetidinones are covalently connected can be produced.

The preparations for oral use can contain one or more sugaring, aromatizing and preserving agents. Tablets contain the active molecule of N-aryl-azetidinone mixed with non-toxic excipients, which are acceptable from the pharmaceutical standpoint. Examples of excipients are inert diluents, such as calcium or sodium carbonate, calcium or sodium phosphate and lactose; agents permitting the granulation and disintegration, e.g. corn starch; fixing agents, e.g. gelatin and starch; and lubricating agents, e.g. talc or magnesium stearate. The tablets may be coated or not (e.g. with the aid of glycerol monostearate or distearate) in order to delay their disintegration and absorption.

The gelatin-coated pills can have a hard gelatin capsule containing the active molecule mixed with an inert solid (e.g. calcium carbonate or kaolin), or a soft gelatin capsule in which the N-aryl-azetidinone is mixed with water or fatty substances (e.g. liquid paraffin).

Aerosols of three types can in particular be envisaged: (a) aqueous aerosols (administered with the aid of atomizers) for which a better solubilization of the N-aryl-azetidinones can be obtained by adding a cosolvent or by forming micelles; (b) pressurized aerosols having e.g. as vector gases chlorinated and fluorinated hydrocarbons of different formulas (or their substitutes) in which the N-aryl-azetidinones can be dissolved or suspended; and (c) powder aerosols with N-aryl-azetidinones in fine particles in e.g. a gelatin capsule.

Aqueous suspensions containing N-aryl-azetidinones and appropriate excipients, with optionally one or more preservatives (e.g. ethyl p-hydroxybenzoate), colouring agents, sugared agents and aromatizing agents can be produced. Among the excipients reference can be made to suspending agents (e.g. methyl cellulose, acacia gum), dispersing and wetting agents, e.g. natural phosphatides (e.g. lecithin) or products for condensing ethylene oxide with various partial esters of fatty acids or aliphatic alcohols. Oily suspensions of the active molecule can be prepared by using a vegetable oil (e.g. olive oil) or a mineral oil (e.g. liquid paraffin), optionally in the presence of sugaring and aromatizing agents, like those given in exemplified manner hereinbefore, together with preservatives (in particular an antioxidant).

Syrups and elixirs could contain sugaring agents (e.g. sucrose or sorbitol), one or more preservatives and also aromatizing agents. Granules or powders which can be suspended in water can be obtained by mixing N-aryl-azetidinones with a wetting or dispersing agent, one or more preservatives and various excipients. Emulsions of N-aryl-azetidinones in water can be produced by using a mineral or vegetable oil and various emulsifying agents, such as e.g. natural gums, natural phosphatides and various esterified fatty acids.

The N-aryl-azetidinones can also be in the form of sterile injectable, aqueous or oily suspensions using suspending or wetting agents of the types described hereinbefore. The solvents, diluents or excipients can e.g. be 1,3-butane diol, an isotonic solution of sodium chloride, water, etc. Suppositories containing the active principle can be prepared with conventional excipients such as polyethylene glycol or e.g. cacao butter. For local uses, it is possible to prepare ointments, creams, jellies, suspensions, solutions, etc. containing the active principle.

Doses of 0.1 to 40 mg/kg of body weight/day can be appropriate. However, the dose for a given patient can depend on a certain number of factors, such as e.g. the effectiveness of the N-aryl-azetidinone in question, the age, weight, administration method, diet, medicamentus interactions and the seriousness of the illness.

These compositions can be used in particular for the treatment of acute or chronic inflammatory processes and degenerative processes, no matter which organ is involved, such as pulmonary emphysema, bronchial inflammation, rheumatoid arthritis, infectious arthritis, rheumatic fever, cutaneous ageing, periodontitis, gingivitis, arterial sclerosis, glomerulonephritis, respiratory distress syndrome, septic shock, Crohn's disease, gout, pancreatis and similar illnesses.

Other characteristics and advantages of the invention can be better gathered from the following examples.

EXAMPLES 1 to 7

These examples disclose the preparation of 3 N-aryl azetidinones of the invention according to the following reaction diagrams:

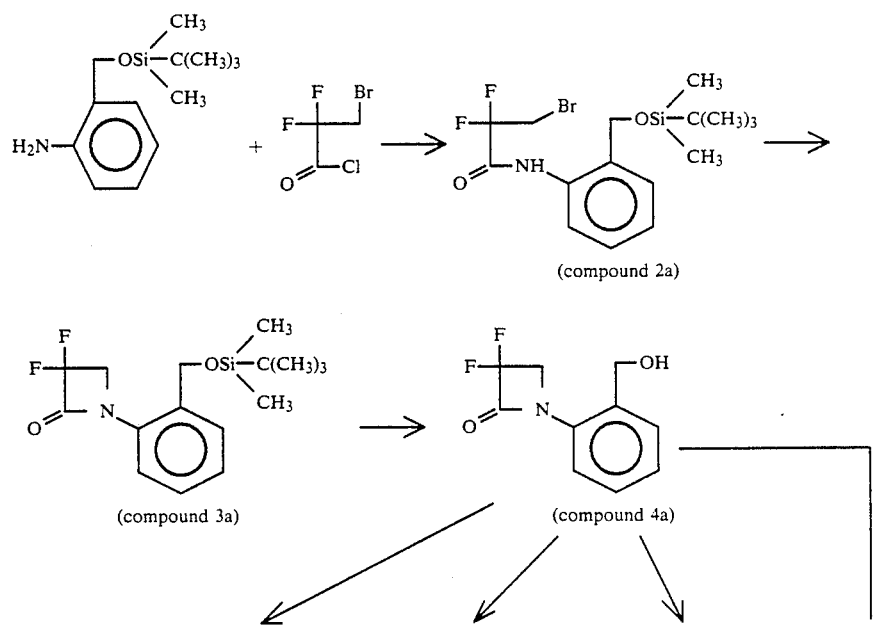

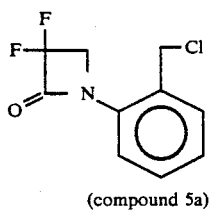 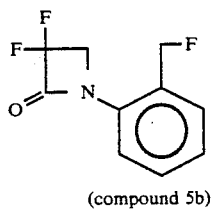 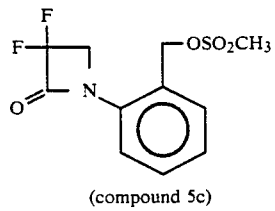

(compound 5a)    (compound 5b)    (compound 5c)

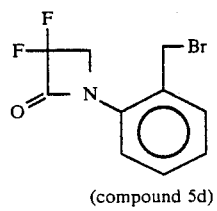

(compound 5d)

EXAMPLE 1

Preparation of N-(tert-2, butyldimethylsilyloxymethyl-phenyl) 2,2-difluoro-3-bromopropionamide (compound 2a)

For this synthesis use is made of tert butyl 2-dimethylsilyloxymethyl-aniline prepared according to the method described by G. Just and R. Zamboni in Canad. J. Chem., 1978, 5b, p. 2720 and 3-bromo-2,2-difluoropropanoyl chloride prepared by the process described by Joyeau et al in Journal of Medicinal Chemistry, 1988, Vol. 31, No. 2, pp. 372–373.

Dropwise addition takes place at 4° C. to a solution of 3-bromo-2,2-difluoropropanoyl chloride (1.1 eq) in dry toluene (2 ml/mmole) of an equimolar mixture of triethylamine and tert butyl-2-dimethylsilyloxymethyl aniline dissolved in toluene (1 ml/mmole). The temperature is maintained at 15° to 20° C. for 35 minutes. The reaction mixture is taken up with ether, washed with a saturated aqueous $NaHCO_3$ solution and then by a saturated aqueous NaCl solution to neutrality. The organic phase is dried on $MgSO_4$ and is evaporated.

The residue obtained is purified by flash chromatography using an ether/pentane mixture with a volume ratio of 1:6. This gives 560 mg of N-(tert-2, butyldimethylsilyloxymethyl-phenyl) 2,2-difluoro-3-bromopropionamide, which corresponds to a 68% yield.

The product obtained has the following characteristics:

Melting point: 36.8° C.

Infrared analysis: $IR(CH_2Cl_2)$: 3400; 1700 cm$^{-1}$.

Analysis by nuclear magnetic resonance: $^1HNMR$ $(CD_3)_2CO$: 0.17 ppm (6H, s); 0.96 (9H, s); 4.16 (2H, t, J=14.07 Hz); 4.94 (2H, s); 7.4 (3H$_{arm}$, m); 8.07 (1H, NH).

$^{19}FNMR \delta(CFCl_3)$: −105.6 ppm (2F, t, J=14.1 Hz).

Elementary analysis:

|   | found | calculated |
|---|-------|------------|
| C | 47.28 | 47.06 |
| H | 5.94  | 5.92  |
| N | 3.37  | 3.43  | m/z: 393–395 (M-14); (350–352); (230–228); 130; 91; 77.

EXAMPLE 2

Preparation of N-(tert butyl-2-dimethylsilyloxymethyl-phenyl)-3,3-difluoro-2-azetidinone (compound 3a)

1.5 mmole of compound 2a obtained in example 1 are dissolved in 9 ml of a mixture of dimethyl formamide (DMF) and $CH_2Cl_2$ with a volume ratio of 1:6. The solution is then added over a period of 40 minutes and at −10° C. to a suspension of NaH (60% dispersed in oil; 3.5 eq) in the same solvent mixture of DMF and $CH_2Cl_2$ (9 ml).

After stirring the reaction mixture for 35 to 45 min., it is rapidly washed with an aqueous saturated ammonium chloride solution to neutrality. Drying takes place on $MgSO_4$ and evaporation takes place on the vane pump. The residue is then purified on a Florisil column using an ethane:pentane mixture (1:12). This gives 303 mg of compound 3a in the form of a white solid corresponding to a 53% yield.

The product obtained has the following characteristics:

melting point: 30.2° C.

Infrared analysis: $IR(CH_2Cl_2)$: 1775 cm$^{-1}$.

Analysis by nuclear magnetic resonance: $^1HNMR$ $(CD_3)_2CO$: 0.13 ppm (6H, s) 0.95 (9H, s); 4.56 (2H, t, J=6.78 Hz); 4.91 (2H, s); 7.46 (4H, arom, m).

$^{19}FNMR—\delta(CFCl_3)$: −117 ppm (2F, t, J=6.50 Hz). m/z: 312 (M-15); 270; 162; 148; 117; 91; 77.

EXAMPLE 3

Preparation of N-(2-hydroxymethyl phenyl) 3,3-difluoro-2-azetidinone (compound 4a)

0.19 mmole of compound 3a is dissolved in 1 ml of acetonitrile and this solution is added dropwise to a 40% $H_2O/HF$ mixture corresponding to 3 eq. Stirring is maintained for 5 min. at ambient temperature, followed by the neutralization of the excess HF by a 5% aqueous $NaHCO_3$ solution.

The mixture is then taken up in ether, the organic phase is rapidly washed with a saturated aqueous NaCl solution, followed by drying on $MgSO_4$ and evaporation. This gives compound 4a in the form of a colourless oil and having the following characteristics:

Infrared analysis: $IR(CH_2Cl_2)$: 3590–3490 ($\nu OH$); 1768 ($\nu_{CO}$) cm$^{-1}$.

Analysis by nuclear magnetic resonance: $^1$HNMR $(CD_3)_2CO$: 4.58 ppm (2H, t, J=6.84 Hz); 4.76 (2H, m); 7.4 (2Harm, m); 7.62 (2Harm, m).
$^{19}$FNMR δ(CFCl$_3$): −112.66 (2F, t, J=6.7 Hz).

EXAMPLE 4

Preparation of N-(2-chloromethyl phenyl)-3,3-difluoro-2-azetidinone (compound 5a)

The reagent used in this case is the Vilsmaier reagent and it is prepared by adding 200 μl of thionyl chloride (SOCl$_2$) to 1 ml of dry dimethyl formamide (DMF) at a temperature of 0° to 4° C. and whilst stirring for 5 min. This gives a SOCl$_2$/DMF reagent. 53 μl of this reagent are then added dropwise to 0.11 mmole of compound 4a dissolved in the minimum of dry DMF. The mixture is then stirred for 20 min. at ambient temperature and vacuum evaporation then takes place of the thionyl chloride. This is followed by the elimination of the DMF with the vane pump. The residue obtained is purified on a silica gel preparative layer using an ether:pentane mixture with a volume ratio of 1:1.5. This gives 13 mg of compound 5a in the form of an oil corresponding to a 51% yield.

The characteristics of this compound are as follows:
IR(CH$_2$Cl$_2$): 1780 cm$^{-1}$ ($\nu_{CO}$).
$^1$HNMR (CD$_3$)$_2$CO: 4.6 ppm (2H, t, J=6.88 Hz); 4.97 (2H, s) 7.63 (4H$_{arm}$, m).
$^{19}$FNMR—δ(CFCl$_3$): −112.8 (2F, t, J=6.7 Hz).
Molecular weight for C$_{10}$H$_8$ClF$_2$NO: found: 231.0263; calculated: 231.02625.
m/z: 231-233 (M$^+$. isotopes Cl); 165-167; 132, 118, 92, 77.

EXAMPLE 5

Preparation of N-(2-fluoromethyl phenyl)-3,3-difluoro-2-azetidinone (compound 5b)

An equimolar quantity of diethylamino sulphur trifluoride (DAST) is added to a solution of compound 4a in dry methylene chloride, at −78° C. and under a dry atmosphere. The reaction mixture is kept at −40° C. for 40 to 50 min. The end of the reaction is monitored on a silica film. After evaporating the solvent, the residue obtained is purified on a preparative layer using an ether:pentane mixture in a ratio of 1:1.5. This gives 11 mg of compound 5b in the form of a colourless oil corresponding to a 41% yield.

The characteristics of this compound are as follows:
IR (CH$_2$Cl$_2$):(1780 m$^-$($\nu_{CO}$).
$^1$HNMR (CD$_3$)$_2$CO): 4.59 (2H, t, J=7.05 Hz); 5.64 (2H, d, J$_{HF}$=47.51 Hz); 7.59 (4H, m).

$^{19}$FNMR—δ(CFCl$_3$): −112.6 ppm (2F, t, J=6.8 Hz); −205(1F, t, J=47.5 Hz).
Molecular weight: found: 215.0562; calculated: 215.05580,
m/z: 215 (M+.); 151; 109.

EXAMPLE 6

Preparation of N-(2-methane sulphonyloxymethyl phenyl)-3,3-difluoro-2-azetidinone (compound 5c).

0.17 mmole of compound 4a is dissolved in 0.8 ml of 2,6-lutidine at 0° C., followed by the addition of 0.18 mmole of sulphonyl methane chloride to said solution. After stirring the reaction mixture for 90 min. at a temperature of 4 to 10° C., the solution is taken up in 1 ml of ether and then washed twice with 0.5 ml of saturated aqueous NaCl solution.

The organic phase is dried on MgSO$_4$ and then evaporated. The oil obtained is purified on a silica preparative layer using an ether:pentane mixture in a ratio of 1:1. This gives 19 mg of compound 5c corresponding to a 39% yield.

The compound has the following characteristics:
IR (CH$_2$Cl$_2$): 1780 cm$^{-1}$ ($\nu$CO); 1350 cm$^{-1}$.
$^1$HNMR ((CD$_3$)$_2$CO): 3.95 (3H, s); 4.6 (2H, t, J=6.31 Hz) 4.95 (2H, s); 7.6 (4H, m).
$^{19}$FNMR (CFCl$_3$): −118 ppm (2F, t, J=6.4 Hz).

EXAMPLE 7

Preparation of N-(2-bromomethyl phenyl)-3,3-difluoro-2-azetidinone (compound 5d)

60 mg (0.28 mmole) of compound 4a are treated with 4 equivalents (0.15 ml) of trimethylsilylbromide at ambient temperature for 35 min. The compound obtained is purified by silica gel plate chromatography using an ether:pentane mixture (1:6). This gives 16 mg of compound 5d corresponding to a 25% yield.

This compound has the following characteristics:
IR: (CH$_2$Cl$_2$): 1775 cm$^{-1}$,
$^1$H NMR (CD$_3$)$_2$CO): 7.37 ppm (4H, m); 4.72 (2H, s); 4.47 (2H, t, J=6.7 Hz).
$^{19}$FNMR (/CFCl$_3$): −115.6 ppm (t, J=6.6 Hz).
Precise weight: (observed/calculated: 274.9760/274.97579).
m/z: 275-277 (M$^+$ isotopes Br); 196(M-Br); 132; 91; 77.

EXAMPLES 8 to 12

These examples correspond to the following reaction diagram:

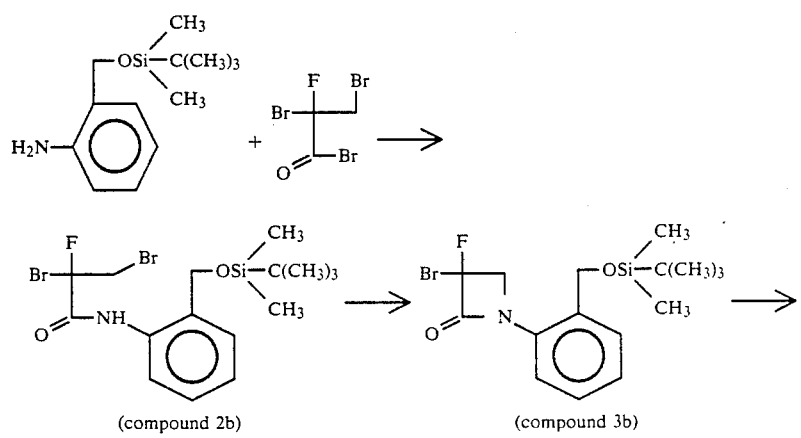

(compound 2b)    (compound 3b)

(compound 4b) → (compound 5a) → (compound 5b)

EXAMPLE 8

Preparation of N-(tert butyl 2-dimethylsilyloxymethyl phenyl)-2,3-dibromo-2-fluoro propanamide (compound 2b)

The same operating procedure as in example 1 is adopted for preparing compound 2b, except that 1.1 eq of 2,3-dibromo-2-fluoro propanoyl bromide is used in place of 1.1 eq of 3-bromo-2,2-difluoropropanoyl chloride. This gives 882 mg of compound 2b corresponding to a yield of 63%.

The product has the following characteristics:
Melting point: 58.2° C.
IR(CH$_2$Cl$_2$): 3290; 1695 cm$^{-1}$.
$^1$HNMR (CD$_3$)$_2$CO): 0.08 (6H, s); 0.87 (9H, s); 4.40 (1H, dd, J=11.49; 9.01 Hz); 4.63 (1H, dd, J=11.52; 31.06 Hz); 7.3 (4H, m); 9.2 (1H, NH).
$^{19}$FNMR δ(CFCl$_3$): −118.6 ppm (ddd; 30; 8 Hz),
Analysis:

|   | Observed | Calculated |
|---|----------|------------|
| C | 41.20    | 40.95      |
| H | 5.08     | 5.16       |
| N | 2.98     | 2.98       | m/z: 410-412-414 (M-57); 252 (M-$^{2Br}$) 130, 91, 77.

EXAMPLE 9

Preparation of N-(tert butyl-2-dimethylsilyloxy-methyl phenyl)-3-bromo-3-fluoro-2-azetidinone (compound 3b)

The operating procedure of example 2 is adopted for preparing compound 3b using 1.5 mmole of compound 2b in place of 1.5 mmole of compound 2a. Following purification on the silica gel preparative layer using a mixture of ethylene acetate:pentane in a ratio of 1:10, 93 mg of compound 3b are obtained in the form of an oil corresponding to a 41% yield.

The product obtained has the following characteristics:
IR(CH$_2$Cl$_2$): 1770 cm$^{-1}$.
$^1$HNMR (CD$_3$)$_2$CO): 0.14 ppm (6H, s); 0.95 (9H, s); 4.6 (1H, dd; J=7.21 (×2)Hz); 4.8 (1H, dd, J=7.36; 9.29 Hz); 4.9 (2H; sys (AB); J=13.93 Hz); 7.35 (2H$_{am}$; m); 7.6 (2H$_{am}$; m).
$^{19}$FNMR δ(CFCl$_3$): −120 ppm (dd; J=7.52 (×2) Hz)
Molecular weight for C$_{16}$H$_{23}$BrFNO$_2$Si: found: 387.0640; calculated: 387.0666.
m/z: 388 (M+. low); (373-375) (332-335); 132; 91.

EXAMPLE 10

Preparation of N-(2-hydroxymethyl phenyl)-3-bromo-3-fluoro-2-azetidinone (compound 4b)

The operating procedure of example 3 is adopted for preparing compound 4b using 0.19 mmole of compound 3b in place of 0.19 mmole of compound 3a. This gives 32 mg of compound 4b in the form of a colourless oil and with a yield of 80%.

The product obtained has the following characteristics:
IR(CH$_2$Cl$_2$): 3570-3460 (νOH): 1765 (νCO)$^{cm-1}$.
$^1$HNMR (CD$_3$)$_2$CO): 4.32 ppm (2H, t, J=5.26 Hz) 4.47 (1H, dd, J=7.29 7.24 Hz); 4.64 (1H, dd, J=7.27; 9.34 Hz).
$^{19}$FNMR—δ(CFCl$_3$): −122.33 (dd, J=7.7; 9.4 Hz).
m/z: 273-275 (M+.(isotopes Br): 216-194, 176, 149, 105, 118, 93, 77, 65.

EXAMPLE 11

Preparation of N-(2-chloromethyl phenyl)-3-fluoro-3bromo-2-azetidinone (compound 5'a)

The operating procedure of example 4 is adopted for preparing compound 5'a using 0.11 mmole of compound 4b in place of 0.11 mmole of compound 4a. This gives 32mg of compound 5'a in the form of a colourless oil corresponding to a 75% yield.

The characteristics of the product obtained are as follows:
IR (CH$_2$Cl$_2$): 1770 cm$^{-1}$ (ν$_{CO}$).
$^1$HNMR (CD$_3$)$_2$CO): 4.47 ppm (1H, dd, J=7.32; 6.93 Hz) 4.73 (1H, dd, J=7.23; 9.37 Hz); 4.85 (2H, dd, sys (AB); J=12 Hz); 7.4(4H$_{arm}$, m).
$^{19}$FNMR—δ(CFCl$_3$)−118.7 ppm / dd, J=7: 9.2 Hz).
Molecular weight for C$_{10}$H$_8$FClBrNO: found: 290.9411; calculated: 290.94624.
m/z: 290-293-295 (M+isotope Cl, Br); 216.167; 132.148.

EXAMPLE 12

Preparation of N-(2-fluoromethyl phenyl)-3-bromo-3-fluoro-2-azetidinone (compound 5'b)

The operating procedure of example 5 is used for preparing compound 5'b using compound 4b in place of compound 4a. This gives 12 mg of compound 5'b in the form of a colourless oil and with a 64% yield.

The product obtained has the following characteristics:
IR (CH$_2$Cl$_2$): 1770 cm$^{-1}$(ν$_{CO}$).
$^1$HNMR (CD$_3$)$_2$CO): 4.55 ppm (1H, dd; J$_{AB}$=7.3; 7.17 Hz) 4.76 (1H, dd, JAB=7.3; 9.06 Hz); 5.5 (2H, d, J=47.55 Hz).
$^{19}$FNMR δ(CFCl$_3$): −204.4 (1F, t, J=47.5 Hz); −118.4 (1F, t, J=7.1; 9.23 Hz).
Molecular weight: found: 274.9763; calculated: 274.97579.
m/z: (275-277) (M+.); 151; 123; 109; 96.

EXAMPLES 13 to 18

These examples relate to the preparation of N-aryl-azetidinones according to the invention using the following reaction diagram:

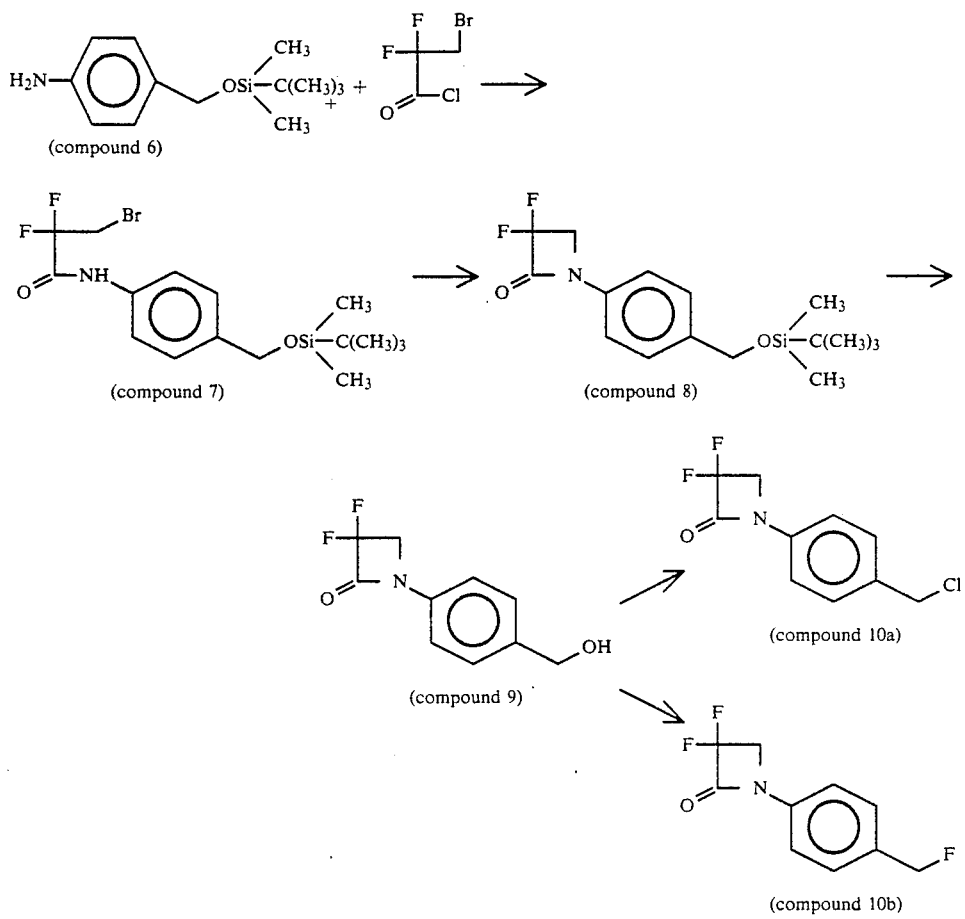

EXAMPLE 13

Preparation of tert butyl 4-dimethylsilyloxymethyl aniline (compound 6)

123 mg (1 mmole) of 4-aminobenzyl alcohol are dissolved in 2 ml of dry DMF and to the solution are added 180 mg (1.2 mmole) of tert butyl dimethylsilyl chloride, followed by 170 mg (2.5 mmole) of imidazole.

Stirring takes place for 40 min. at ambient temperature and then the DMF is evaporated with the vane pump. The residue is taken up in 10 ml of ether and the ethereal phase washed with 4×4 ml of water, followed by drying on MgSO$_4$ and evaporation. The oil obtained is purified by flash chromatography using an ether:pentane mixture in a volume ratio of 3:2. This gives 173 mg of compound 6 corresponding to a 73% yield.

The product obtained has the following characteristics:

IR (CH$_2$Cl$_2$): 3430–3380; 2800; 1610; 1510; 1100 cm$^{-1}$.

$^1$HNMR (CD$_3$)$_2$CO): 0.05 ppm (6H, s); 0.85 (9H, s); 4.4 (2H, NH$_2$ s wide); 4.55 (2H, s); 6.35 (2H, d, J=8.8 Hz); 6.95 (2H, d, J=8.7 Hz).

EXAMPLE 14

Preparation of N-(tert butyl-4-dimethylsilyloxymethyl phenyl)-2,2-difluoro-3-propionamide (compound 7)

The same operating procedure as in example 1 is used employing compound 6 is place of tert butyl-2-dimethylsilyloxymethyl aniline. This gives 230 mg of compound 7 corresponding to a 70% yield.

The characteristics of the product obtained are as follows:

Melting point: 57.3° C.

IR(CH$_2$Cl$_2$): 3400; 1700 cm$^{-1}$.

$^1$HNMR (CD$_3$)CO): 0.17 ppm(6H, s); 1 (9H, s); 4.16 (2H, t, J=14.3 Hz); 4.82 (2H, s); 7.43 (2H$_{am}$; d; J=8.58 Hz); 7.8 (2H, d, J=8.53 Hz).

$^{19}$FNMR—δ(CFCl$_3$): −120.8 ppm(t; J=14 Hz).

Molecular weight for C$_{16}$H$_{24}$F$_2$BrNO$_2$Si:
found: 407.0729;
calculated: 407.07283.

Elementary analysis:

|   | found | calculated |
|---|---|---|
| C | 47.76 | 47.06 |
| H | 5.99 | 5.92 |
| N | 3.33 | 3.43 | m/z: 407 (M$^+$·) weak; (352–350) isotopes Br; (230–228); 106, 90.

EXAMPLE 15

Preparation of N-(tert butyl-4-dimethylsilyloxymethylphenyl)-3,3-difluoro-2-azetidinone (compound 8)

The operating procedure of example 2 is adopted for preparing compound 8 using 1.5 mmole of compound 7 in place of 1.5 mmole of compound 2a. Following purification on a Florisil column using an ether: pentane mixture with a volume ratio of 1:6, 72mg of compound 8 are obtained corresponding to a 51% yield. This compound is a white solid melting at 48° C.

The product obtained has the following characteristics:

IR (CH$_2$Cl$_2$): 1770 cm$^{-1}$,
$^1$HNMR (CD$_3$)$_2$CO): 0.2 ppm (6H, s); 1(9H, s); 4.49 (2H, t, J=6.42 Hz); 4.87 (2H, s); 7.55 (4H, m).
$^{19}$FNMR δ(CFCl$_3$): −111.6 ppm (2F, t, J=6.4 Hz).
Molecular weight: found: 327.1471;
calculated: 327.14661, m/z: 327 (M+·); 312; 270; 196; 168.

EXAMPLE 16

Preparation of N-(4-hydroxymethyl phenyl)-3,3-difluoro-2-azetidinone (compound 9)

The operating procedure of example 3 is adopted for preparing compound 9 from compound 8 using 0.19 mmole of compound 8 in place of 0.19 mmole of compound 3a. This gives 42 mg of compound 9 in the form of a solid, which corresponds to an 82% yield.

The product obtained has the following characteristics:

Melting point: 124° C.
IR (CH$_2$Cl$_2$): 3580–3490 (νOH): 1768 (νCO) cm$^{-1}$.
$^1$HNMR (CD$_3$)$_2$CO): 4.68 ppm (2H, d, J=5.7 Hz); 4.45 (2H, t, J=6.32 Hz); 4.35 (1H, t, J=5.76 Hz); 7.5 (4H$_{am}$; s).
$^{19}$FNMR—δ(CFCl$_3$): −111.6 ppm (2F, t, J=6.4 Hz).
Molecular weight for C$_{10}$H$_9$F$_2$NO$_2$:
found: 213.0604;
calculated: 213.06014.
m/z: 213(M+·); 149; 106.

EXAMPLE 17

Preparation of N-(4-chloromethyl phenyl)-3,3-difluoro-2-azetidinone (compound 10a)

The operating procedure of example 4 is followed for the preparation of compound 10a from compound 9 using 0.11 mmole of compound 9 in place of 0.11 mmole of compound 4a. This gives 16 mg of compound 10a in the form of a white solid corresponding to a 55% yield.

The compound obtained has the following characteristics:

Melting point: 93° C.
IR (CH$_2$Cl$_2$): 1770 cm$^{-1}$(CO).
$^1$HNMR (CD$_3$)$_2$CO): 4.48 (2H, t, J=6.53 Hz); 4.79(2H, s); 7.57 (4H$_{arm}$, d; J=8.6 Hz).
$^{19}$FNMR—(CFCl$_3$): −111.5 ppm (2F, t, J=6.6 Hz).
Molecular weight for C$_{10}$H$_8$F$_2$ClNO: found: 231.0260; calculated: 231.02625.
m/z: 231–233 (M+· isotope Cl): 196; 167; 169; 168; 132 118; 90; 77.

EXAMPLE 18

Preparation of N-(4-fluoromethyl phenyl)-3,3-difluoro-2-azetidinone (compound 10b)

The operating procedure of example 5 is used for preparing compound 10b from compound 9, the latter being used instead of compound 4a. This gives 16 mg of compound 10b in the form of a solid corresponding to a 38% yield.

The product obtained has the following characteristics:

Melting point: 104° C.
IR (CH$_2$Cl$_2$): 1770 cm$^{-1}$(CO).
$^1$HNMR—(CD$_3$)CO): 4.49 ppm (2H, t, J=6.49 Hz); 5.46 (2H, d, J=48 Hz); 7.58 (4H, s).
$^{19}$FNMR (CFCl$_3$): −111.5 ppm (2F, t, J=6.6 Hz); −200.39 (1F, t, J=48 Hz).
Molecular weight: found: 215.0559; calculated: 215.05580.
m/z: 215 (M+·); 151; 106; 109.

EXAMPLES 19 TO 22

These examples illustrate the preparation of N-aryl-azetidinones according to the invention using the following reaction diagram:

EXAMPLE 19

Preparation of N(tert butyl-2-dimethylsilyloxy-methyl phenyl)-2,2,3-trichloro propionamide (compound 2e)

For this synthesis, use is made of tert buty-2-dimethylsilyl-oxymethyl aniline prepared according to the method described by G. Just and R. Zamboni in Canad. J. Chem. 1978, 5b, p.2720 and trichloropropanoyl chloride prepared in the following way.

Firstly 2,2,3-trichloropropionitrile is prepared by adding chlorine to α-chloroacrylonitrile, as descibed by H. Brintzinger et al in Angew. Chemie, 1948, 60,p.311 and then the 2,2,3-trichloropropionitrile undergoes acid hydrolysis with 60% $H_2SO_4$ at 125° C. and for 5 hours in order to obtain the corresponding acid, as described by H. Laato in Suomen Kemistilehti, 1968, 41B, p.266. The acid is then treated by $SOCl_2$ in the presence of a catalytic quantity of DMF at 40° to 50° C.and for 1 hour, which gives 2,2,3-trichloropropanoyl chloride, which is distilled at 50° C. under 2700 Pa (20 mm of Hg),the yield being 66%.

This compound has the following characteristics:
IR $(CH_2Cl_2)$: 1800 1770 cm$^{-1}$(intense band).
$^1$HNMR $(CDCl_3)$: 4.4 ppm (2H, s).

The same operating procedure as in example 1 is used for preparing N-(tert butyl-2-dimethylsilyloxymethyl phenyl)-2,2,3-trichloropropionamide from tert butyl-2-dimethylsilyloxymethyl aniline and 2,2,3,-trichloropropanoyl chloride. This gives 814 mg of compound 2e corresponding to a 70% yield.

The compound has the following characteristics:
White solid: m.p. 41° C.; IR$(CH_2Cl_2)$; 3300; 1690; 1585 cm$^{-1}$
$^1$HNMR: 10.25(1H,NH); 8.25(1H,d);7.35(2H,m); 4.8(2H,s); 4.2(2H,s); 0.95(9H,s); 0.15(6H,s).
m/z: 382-384 (M-14); 338-340; 268; 200;192; 164; 132 93; 75; 29.
Micro analysis:

|   | found | calculated % |
|---|---|---|
| C | 48.32 | 48.43 |
| H | 6.32 | 6.10 |
| N | 3.6 | 3.53 |

EXAMPLE 20

Preparation of N-(tert butyl-2-dimethylsilyloxymethyl phenyl)-3,3-dichloro-2-azetidinone (compound 3e)

The same operating procedure as in example 2 is adopted for preparing compound 3e from compound 2e. The product obtained is purified by flash chromatography using an ether:pentane mixture (1:10). This gives compound 3e in the form of a white solid with a 59% yield.

This compound has the following characteristics:
IR$(CH_2Cl_2)$: 1770 cm$^{-1}$ ($\nu co\beta$lactame).
$^1$HNMR $(CDCl_3)$; 7.5(4H,m); 4.8(2H,s); 4.5(2H,s); 0.95(9H,s); 0.15(6H,s).
Precise weight: (observed/calculated: 359.087/359.0875).
m/z: 344-346; 302-304; 206; 192; 132; 93; 73; 29;
Micro analysis:

|   | found | calculated % |
|---|---|---|
| C | 53.24 | 53.33 |
| H | 6.62 | 6.43 |
| N | 3.67 | 3.89 |

EXAMPLE 21

Preparation of N-(2-hydroxymethyl phenyl) 3,3dichloro-2-azetidinone (compound 4e)

The operating procedure of example 3 is used for preparing compound 4e from compound 3e. This gives compound 4e in the form of a colourless oil with a 70% yield. This compound has the following characteristics:
IR$(CH_2Cl_2)$:3580-3480 ($\gamma$OH cm$^{-1}$; 1765 ($\gamma$co lactame) cm$^{-1}$.
$^1$H NMR $(CDCl_3)$: 7.45 ppm (4H,m); 4.75(2H,s); 4.5(2H,s); 3(1H,s).

EXAMPLE 22

Preparation of N-(2-chloromethyl phenyl)-3,3-di-chloro-2-azetidinone (compound 5e)

The operating procedure of example 4 is used for preparing compound 5e from compound 4e. The product obtained is purified by silica gel chromatography using an ether:pentane mixture (1:5). This gives compound 5e in the form of a white solid with a yield of 67%. This compound has the following characteristics:
F: 79° C.
IR: $(CH_2Cl_2)$: 1770 cm$^{-1}$.
$^1$H NMR $(CDCl_3)$: 7.5 (4H,s); 4.8 (2H,s); 4.5(2H,s);
Precise weight: (found: calculated: 262.9675/262.96715).
m/z: 263-261 (isotopes Cl); 169-167; 132; 91; 77; 40; 29.
Micro analysis:

|   | found | calculated % |
|---|---|---|
| C: | 45.67 | 45.4 |
| H: | 3.12 | 3.05 |
| N: | 5.06 | 5.3 |

EXAMPLE 23

Preparation of N-(2-bromomethyl phenyl)-3,3-difluoro-2-azetidinone (compound 5d)

This example uses another process for preparing compound 5d of example 7. This process corresponds to the following reaction diagram:

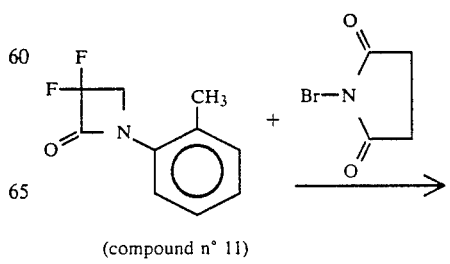

(compound n° 11)

21

-continued

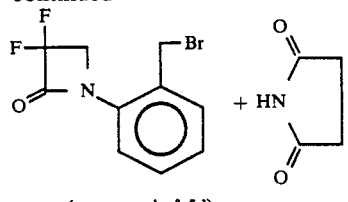

(compound n° 5d)

The starting compound 11 is prepared from 3-bromo-2,2-difluoro propanoyl chloride used in example 1 and ortho-toluidine by cyclization following the operating procedure of examples 1 and 2 for preparing compound 3a.

24 mg (0.12 mmole) of compound 11 are dissolved in 20 ml of $CCl_4$ and 21 mg (0.12 mmole) of N-bromosuccinimide and a catalytic quantity of benzoyl peroxide are added. After refluxing (78° C.) for 1 hour and illuminating with a 150 watt lamp, hot filtering takes place of the succinimide formed. The filtrate is then cooled and evaporated in vacuo, which gives a solid product, purified by silica gel chromatography. This gives 20mg of compound 5d corresponding to a 62% yield.

EXAMPLE 24

The properties of the N-aryl-azetidinones obtained in examples 4, 5, 6, 7, 11, 17, 22 and 23 are checked and in particular their deactivation capacity for porcine pancreatic elastase (PPE) and human leucocytic elastase (HLE) using the methods of Kitz and Wilson for HLE in the case of compounds 5a, 5c, 5d, 5e, 5a' and 10a, the method of Kitz and Wilson for PPE in the case of compounds 5a, 5c, 5e and 10a and the method of Hart and O'Brian for PPE in the case of compounds 5a and 5'a. All the kinetic measurements are carried out at 37° C. and at a pH of 8 with a 0.1M tris buffer (PPE) or a 0.1M tris buffer, Brij 0.01%, $NaN_3$ 0.02% (HLE) (pH 7.5 for compound 5d).

The method of Hart and O'Brian was published in 1973 in Biochemistry, Vol. 12, pp. 2940–2945 and that of Kitz and Wilson in 1962 in J. Biol. Chem., Vol. 237, pp. 3245–3249.

In this way the first order constant ki is determined for the formation of the deactivated enzyme and the dissociation constant Ki of the enzyme-inhibitor complex. The ki: Ki ratio is the apparent second order constant characterizing the deactivation.

The results obtained are given in the following table.

On the basis of these results, it can be seen that compounds 5a, 5c, 5'a, and 10 a deactivate PPE and HLE.

On testing compounds 5, 5c, 5'a'under identical conditions as chymotrypsin or trypsin inhibitors, it can be seen that they have no action on these enzymes.

EXAMPLE 25

This example used for testing the properties of compounds 5b and 10b with respect to elastase and it can be seen that these compounds are elastase substrates, but that they are not inhibitors. Thus, the nature of the $R^3$ substituent has a significant influence on the properties of the product obtained.

EXAMPLE 26

The effect of compound 5on the degradation of elastin, the natural substrate of elastase in the human organism was tested. The elastase, previously treated by compound 5a, lost its capacity to degrade elastin. Compounds 5a, 5c and 5'a remain capable of deactivating elastase previously incubated for 30 min. in the presence of an elastin excess (2mg).

The acute toxicity of compound 5a researched on male and female mice exceeds 200 mg/kg.

TABLE

| Compound | $R^1$ | $R^2$ | $R^3$ | PPE ki ($s^{-1}$) | PPE Ki (M) | PPE ki/Ki ($M^{-1}s^{-1}$) | HLE ki ($s^{-1}$) | HLE Ki (M) | HLE ki/Ki ($M^{-1}s^{-1}$) |
|---|---|---|---|---|---|---|---|---|---|
| ORTHO | | | | | | | | | |
| 5a | F | F | Cl | 0.031 | $3 \cdot 10^{-5}$ | 1033 | $5 \cdot 10^{-3}$ | $1.66 \cdot 10^{-5}$ | 301 |
| 5c | F | F | $OSO_2CH_3$ | 0.017 | $4.8 \cdot 10^{-5}$ | 354 | 0.05 | $5 \cdot 10^{-4}$ | 100 |
| 5'a | F | Br | Cl | 0.048 | $0.85 \cdot 10^{-5}$ | 5647 | 0.37 | $1.17 \times 10^{-3}$ | 316 |
| 5d | F | F | Br | | | | | | 40 |
| 5e | Cl | Cl | Cl | 0.028 | $5.9 \cdot 10^{-4}$ | 47 | 0.03 | $5 \cdot 10^{-4}$ | 60 |
| PARA | | | | | | | | | |
| 10a | F | F | Cl | 0.075 | $6.6 \cdot 10^{-4}$ | 113 | | | ~1.2 |

We claim:

1. N-aryl-azetidinones according to the formula:

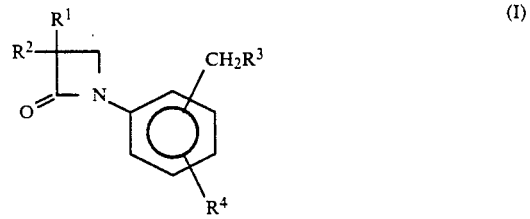

(I)

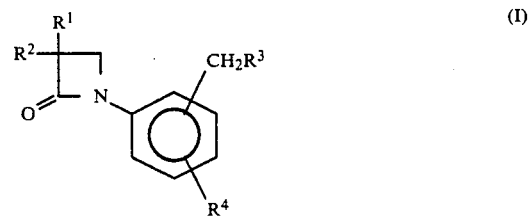

(I)

in which $R^1$ and $R^2$, which can be the same or different, represent an atom of F, Br, Cl or I, or a radical of formula $CF_3$, $COOR^5$, CN, $CONHR^5$ or $COR^5$ with $R^5$ representing an alkyl or aryl radical, $R^3$ represents a chlorine, bromine or iodine atom, or a radical of formula $OC(O)R^6$, $OSO_2R^6$, $OP(O)R^6_2$ or $S^+R^6_2 X^-$ with $R^6$ representing an alkyl, perfluoroalkyl or aryl radical and $X^-$ a halide, and $R^4$ represents a hydrogen atom or a radical chosen from among the alkyl radicals and the radicals of formula $COOR^7$, $CONHR^7$, $NO_2$, $CF_3$, CN, $SO_2R^7$, $(CH_2)_nOR^7$ and $OR^7$ with $R^7$ representing a hydrogen atom or an alkyl or aryl radical and n being an integer between 1 and 18.

2. N-aryl-azetidinone according to claim 1, characterized in that —CH$_2$R$^3$ is in the ortho or para position relative to N.

3. N-aryl-azetidinone according to claim 2, characterized in that —CH$_2$R$^3$ is in the ortho position relative to N.

4. N-aryl-azetidinone according to any one of the claims 1 to 3, characterized in that R$^4$ is a hydrogen atom.

5. N-aryl-azetidinone according to claim 1, characterized in that R$^3$ represents F, Cl, Br or OSO$_2$CH$_3$.

6. N-aryl-azetidinone according to claim 5, characterized in that R$^1$ and R$^2$ represent F.

7. N-aryl-azetidinone according to claim 5, characterized in that R$^1$ represents F and R$^2$ represents Br.

8. N-aryl-azetidinone according to claim 5, characterized in that R$^1$ and R$^2$ represent Cl.

9. Pharmaceutical composition comprising a pharmaceutically acceptable carrier incorporating an elastase inhibitor, characterized in that said elastase inhibitor is a N-aryl-azetidinone of formula:

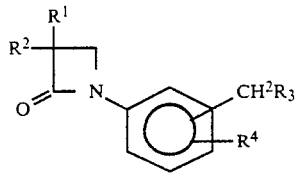

in which
R$^1$ and R$^2$, which can be the same or different, stand for an atom of F, Br, Cl or I, or a radical of formula CF$_3$, COOR$^5$, CN, CONHR$^5$ or COR$^5$ with R$^5$ representing an alkyl or aryl radical,
R$^3$ represents a chlorine, bromine or iodine atom, or a radical of formula OC(O)R$^6$, OSO$_2$R$^6$, OP(O)R$^6_2$ or S+R$^6_2$X— with R$^6$ representing an alkyl, perfluoroalkyl or aryl radical and X— a halide, and
R$^4$ represents a hydrogen atom or a radical chosen from among the alkyl radicals and radicals of formula COOR$^7$, CONHR$^7$, NO$_2$, CF$_3$, CN, SO$_2$R$^7$, (CH$_2$)$_n$OR$^7$ and OR$^7$ with R$^7$ representing a hydrogen atom or an alkyl or aryl radical and n being an integer between 1 and 18.

10. Pharmaceutical composition according to claim 9, characterized in that R$^4$ is a hydrogen atom and R$^3$ is Cl, Br or OSO$_2$CH$_3$.

11. Pharmaceutical composition according to either of the claims 9 and 10, characterized in that R$^1$ is F and R$^2$ is F or Br.

12. Pharmaceutical composition according to either of the claims 9 and 10, characterized in that R$^1$, R$^2$ and R$^3$ represent Cl.

13. N-aryl-azetidinone according to claim 6, 7 or 8, characterized in that R$^4$ is a hydrogen atom.

* * * * *